(12) United States Patent
Giraud et al.

(10) Patent No.: US 8,431,720 B2
(45) Date of Patent: Apr. 30, 2013

(54) INDOLESULFONYL PROTECTING GROUPS FOR PROTECTION OF GUANIDINO AND AMINO GROUPS

(75) Inventors: Matthieu Giraud, Sion (CH); Fernando Albericio, Barcelona (ES); Albert Isidro Liobet, Barcelona (ES); Mercedes Alvarez Domingo, Sant Joan Despi (ES)

(73) Assignee: Lonza Ltd., Visp (CH)

( * ) Notice: Subject to any disclaimer, the term of this patent is extended or adjusted under 35 U.S.C. 154(b) by 123 days.

(21) Appl. No.: 12/990,934

(22) PCT Filed: May 5, 2009

(86) PCT No.: PCT/EP2009/003210
§ 371 (c)(1),
(2), (4) Date: Nov. 3, 2010

(87) PCT Pub. No.: WO2009/135645
PCT Pub. Date: Nov. 12, 2009

(65) Prior Publication Data
US 2011/0060125 A1   Mar. 10, 2011

Related U.S. Application Data

(60) Provisional application No. 61/095,709, filed on Sep. 10, 2008.

(30) Foreign Application Priority Data

May 5, 2008 (EP) .................................... 08008418

(51) Int. Cl.
*C07D 209/30* (2006.01)

(52) U.S. Cl.
USPC ............................................ 548/484; 930/20

(58) Field of Classification Search ................... 548/484
See application file for complete search history.

(56) References Cited

U.S. PATENT DOCUMENTS

2003/0220319 A1   11/2003   Greenhouse et al.

FOREIGN PATENT DOCUMENTS

WO          0157045 A1     8/2001

OTHER PUBLICATIONS

Lu et al., "Design and Synthesis of Human Immunodeficiency Virus Entry Inhibitors: Sulfonamide as an Isostere for the Alpha-Ketoamide Group", Journal of Medical Chemistry, vol. 50, pp. 6535-6544; 2007.
Carpino et al., "The 2,2,4,6,7-Pentamethyldihydrobenzofuran-5 sulfonyl Group (Pbf) as Arginine Side Chain Protectant", Tetrahedron Letters, vol. 34, No. 49, pp. 7829-7832; 1993.
Lowe et al., "Synthesis of Heterocyclic Sulfonylureas", Journal of Heterocyclic Chem, vol. 33, pp. 763-766; 1996.

*Primary Examiner* — Shawquia Young
(74) *Attorney, Agent, or Firm* — Hoffmann & Baron, LLP

(57) ABSTRACT

The invention relates to indolesulfonyl halogenides which are useful for the protection of organic compounds comprising at least one guanidino moiety and/or at least one amino group. The invention further relates to a process for their preparation and their use as protecting reagents. The invention also relates to the process for the protecting reaction and to the protected compounds thereof.

10 Claims, No Drawings

INDOLESULFONYL PROTECTING GROUPS FOR PROTECTION OF GUANIDINO AND AMINO GROUPS

This application is the U.S. National Phase of, and Applicants claim priority from, International Application Number PCT/EP2009/003210 filed 5 May 2009, European Patent Application bearing Serial Number 08008418.9 filed 5 May 2008 and U.S. Provisional Patent Application No. 61/095,709 filed 10 Sep. 2008, which are incorporated herein by reference in their entirety.

BACKGROUND OF THE INVENTION

The present invention relates to compounds which are useful for the protection of organic compounds comprising at least one guanidino moiety and/or at least one amino group. The invention further relates to a process for the preparation of these compounds and to their use as protecting reagents. The invention also relates to the process for the protecting reaction and to the protected compounds thereof.

Suitable protection of a guanidino moiety is still an unsolved problem in chemistry because of the difficulty to remove the known protecting groups. This applies particularly to peptide chemistry as the natural amino acid arginine, bearing a guanidino moiety, is of great importance for the preparation of numerous drug substances. During the coupling reaction, guanidino protection of arginine is necessary to avoid acylation potentially followed by deguanidation, thus rendering undesired ornithine and δ-lactam formation.

Depending on the coupling strategy, the most commonly used protecting groups for arginine are p-toluenesulfonyl (Tos), 2,2,5,7,8-pentamethylchroman-6-sulfonyl (Pmc) and 2,2,4,6,7-pentamethyldihydrobenzofuran-5-sulfonyl (Pbf). However, these protecting groups are too acid-stable, thus requiring harsher removal conditions and a longer removal time. Therefore, the known guanidino protecting groups are prone to form by-products on their removal. Particularly problematic is their cleavage in peptides with multiple arginine residues or in peptides containing tryptophan. Carpino et al. (Tetrahedron Letters 1993, Vol. 34, No. 49, 7829-7832) compare the Pbf protecting group with the Pmc protecting group when used for arginine side chain protection.

WO 01/57045 discloses tricyclic sulfames obtained via benzofuran-, benzothiophene- and indole-intermediates.

Löwe et al. describe the synthesis of heterocyclic sulfonylureas, which for example comprise an indole moiety (J. Heterocyclic Chem., 1996, 33, 763-766).

It is an object of the present invention to provide a compound which easily protects the guanidino moiety of an organic compound and which can be easily removed.

DESCRIPTION OF THE INVENTION

The object described above is achieved by the compounds of claim 1, which can be prepared by the process of claim 5 and which is used according to claim 9 in the protection process of claim 12 affording compounds of claim 16.

In one aspect, the present invention relates to a compound of formula

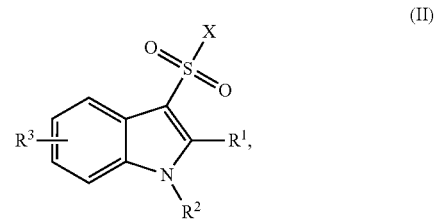

(II)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and X is chlorine or bromine.

Here and as follows, the term "$C_{1-n}$ alkyl" is to be understood to mean any linear or branched alkyl group containing 1 to n carbon atoms. For example the term "$C_{1-6}$ alkyl" comprises groups such as methyl, ethyl, propyl, isopropyl, butyl, isobutyl, sec-butyl, tert-butyl, pentyl, isopentyl (3-methylbutyl), neopentyl (2,2-dimethylpropyl), hexyl, isohexyl (4-methylpentyl) and the like.

Accordingly, the term "$C_{1-n}$ alkoxy" means a group composed of a $C^{1-n}$ alkyl group as defined above and an oxygen atom linked by a single covalent bond.

In the same manner, the term "$C_{1-6}$ alkylthio" means a group composed of a $C_{1-6}$ alkyl group as defined above and an sulfur atom linked by a single covalent bond.

Here and as follows the term "halogen" means fluorine, chlorine, bromine and iodine.

Favourably, the present invention relates to a compound of formula (II), wherein $R^1$, $R^2$, $R^3$ and X are as defined above with the exception of 1-methylindole-3-sulfonyl chloride.

In a preferred embodiment, $R^1$ and $R^2$ are independently $C_{1-4}$ alkyl, $C_{1-4}$ alkoxy or $C_{1-4}$ alkylthio; $R^3$ is hydrogen or halogen; and X is chlorine or bromine.

In a particular embodiment, both $R^1$ and $R^2$ are methyl; $R^3$ is hydrogen; and X is chlorine being 1,2-dimethylindole-3-sulfonyl chloride. For the sake of convenience, this compound will be abbreviated as MIS-Cl.

In a further aspect of the present invention, the compound of formula (II) is prepared by a process comprising the step of reacting a compound of formula

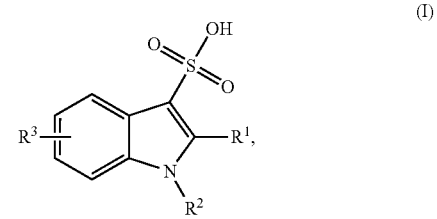

(I)

wherein $R^1$, $R^2$ and $R^3$ are as defined above, or a salt thereof, with oxalyl chloride or oxalyl bromide.

In a preferred embodiment, $R^1$ and $R^2$ are independently $C_{1-4}$ alkyl, $C_{1-4}$ alkoxy or $C_{1-4}$ alkylthio, and $R^3$ is hydrogen or halogen.

In a more preferred embodiment, both $R^1$ and $R^2$ are methyl and $R^3$ is hydrogen.

In the process for the preparation of the compound of formula (II) both the acidic form and the salt form of the compound of formula (I) may be used as reagent. Any salt form of the compound of formula (I) can be applied. Suitable salts are e.g. the sodium salt, the potassium salt, the calcium salt and the pyridinium salt.

In a preferred embodiment, the reaction is performed with the pyridinium salt of the compound of formula (I).

Preferably, oxalyl chloride is applied for the reaction.

For the preparation process, any suitable solvent or mixtures of suitable solvents may be applied. Suitable solvents are solvents which do not react with the reactants or with the product and which dissolve the reactants to a sufficient extent. Examples of suitable solvents are dichloromethane, chloroform, carbon tetrachloride, tetrahydrofuran and 1,4-dioxane. Preferably, dichloromethane is used as solvent.

The reaction may also be performed without a solvent.

Expediently, the reaction is performed in the presence of N,N-dimethylformamide.

In an additional aspect of the present invention, the compound of formula

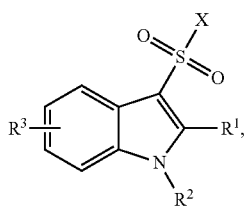

(II)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and X is chlorine or bromine, is used for the protection of an organic compound which comprises at least one guanidino moiety and/or at least one amino group.

In a preferred embodiment, the organic compound is an optionally resin-bound peptidic compound which is optionally side chain protected and/or protected at a free terminus; $R^1$ and $R^2$ are independently $C_{1-4}$ alkyl, $C_{1-4}$ alkoxy or $C_{1-4}$ alkylthio, and $R^3$ is hydrogen or halogen.

Here and in the following, the term "peptidic compound" is to be interpreted in a wide manner as defined hereafter. Therefore, the term "peptidic compound" is to be understood to mean any compound of one of the following categories (a) to (d):

(a) A peptide, i.e. a compound produced by formation of an amide bond between a carboxyl group of one amino acid and an amino group of another. The amide bond is typically formed between C-1 of one amino acid and N-2 of another (eupeptide bond), but a compound with residues linked by other amide bonds (isopeptide bonds) is also meant to be covered by the term "peptidic compound". Oligopeptides consisting of two to fifteen amino acid residues and polypeptides consisting of sixteen to about fifty amino acid residues are typical peptides of this category. The amino acid residues may be any natural or unnatural amino acids. An example for a peptide is H-Arg-Val-OH.

(b) An amino acid, which may not only be an amino acid commonly found in proteins (natural α-amino acid) but also any unnatural amino acid. Examples are H-Ala-OH (natural amino acid) and homoarginine (unnatural amino acid).

(c) A derivative of a peptide, meaning a peptide in which one or more of the amino acid residues have been chemically modified, e.g. by acylation, alkylation, ester formation or amide formation. Examples are Ac-Phe-Arg-Gly-Ala-Val-OH (SEQ ID NO 5), H-Phe-Arg-Gly-Ala-Val-$NH_2$ (SEQ ID NO 6) and H-Arg-Gly-Ala-Gly-Gly-Lys($N^\epsilon$-tetradecanoyl)-Ala-Gly-Gly-OH (SEQ ID NO 7).

(d) A derivative of an amino acid, meaning an amino acid which has been chemically modified, e.g. by acylation, alkylation, ester formation or amide formation. An example is H-Ala-OMe.

In another preferred embodiment, the peptidic compound comprises at least one guanidino moiety and optionally at least one amino group, the guanidino moiety being part of an arginine, homoarginine or norarginine residue. More preferably, said guanidino moiety is part of an arginine or homoarginine residue. Even more preferably, the peptidic compound is Z-Arg-OH.

The prefix "homo" to the name of a common amino acid (like homoarginine) means that said amino acid contains one additional methylene group in the carbon chain.

In contrast, the prefix "nor" to the name of a common amino acid (like norarginine) denotes removal of one methylene group in the carbon chain.

In another preferred embodiment, the peptidic compound comprises at least one amino group and optionally at least one guanidino moiety, said at least one amino group(s) being the N-terminal amino group or part of the side chain of an amino acid residue.

More preferably, the amino group to be protected is the N-terminal amino group of said peptidic compound. Most preferably, the peptidic compound is H-Ala-OMe.

Also more preferably, the amino group to be protected is part of the side chain of an amino acid residue of said peptidic compound. Even more preferably, said amino group is part of a lysine, homolysine or norlysine residue. Most preferably, said peptidic compound is Z-Lys-OH.

In another aspect, the present invention relates to a process for the protection of an organic compound, which comprises at least one guanidino moiety and/or one amino group, said process comprising the reaction of said compound with the compound of formula

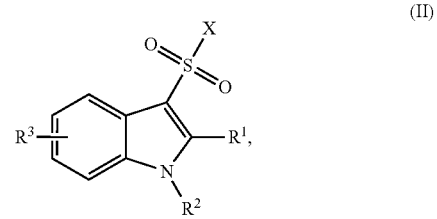

(II)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and X is chlorine or bromine, thus affording a compound, which comprises at least one moiety of the formula

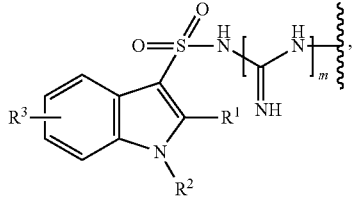

(III)

wherein $R^1$, $R^2$ and $R^3$ are as defined above and m is 0 or 1.

In one embodiment, m is 1, thus affording a compound, which comprises at least one moiety of the formula

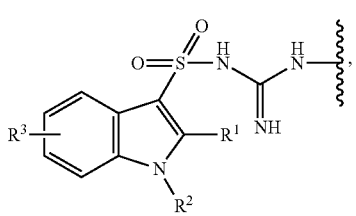

(IV)

wherein $R^1$, $R^2$ and $R^3$ are as defined above.

In another embodiment, m is 0, thus affording a compound, which comprises at least one moiety of the formula

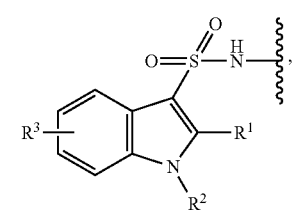

(V)

wherein $R^1$, $R^2$ and $R^3$ are as defined above.

In a preferred embodiment, $R^1$ and $R^2$ are independently $C_{1-4}$ alkyl, $C_{1-4}$ alkoxy or $C_{1-4}$ alkylthio, $R^3$ is hydrogen or halogen. In one embodiment, m is 1 and in another embodiment, m is 0.

In a more preferred embodiment, $R^1$ and $R^2$ are methyl, $R^3$ is hydrogen and X is chlorine. In one embodiment, m is 1; and in another embodiment, m is 0.

In another preferred embodiment, the organic compound is an optionally resin-bound peptidic compound which is optionally side chain protected and/or protected at a free terminus, thus affording said peptidic compound, which comprises at least one moiety of the formula

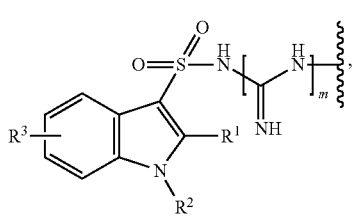

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; and $R^3$ is hydrogen, halogen, $C_{1-6}$ alkyl, $C_{1-6}$ alkoxy, $C_{1-6}$ alkylthio, phenyl or benzyl; and m is 0 or 1.

Preferably, $R^1$ and $R^2$ are independently $C_{1-4}$ alkyl, $C_{1-4}$ alkoxy or $C_{1-4}$ alkylthio and $R^3$ is hydrogen or halogen. Most preferably, $R^1$ and $R^2$ are methyl and $R^3$ is hydrogen.

In a preferred embodiment, said peptidic compound comprises at least one guanidino moiety being part of an arginine, homoarginine or norarginine residue, preferably being part of an arginine or homoarginine residue, thus affording said peptidic compound, which comprises at least one moiety of the formula (III), wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; and $R^3$ is hydrogen, halogen, $C_{1-6}$ alkyl, $C_{1-6}$ alkoxy, $C_{1-6}$ alkylthio, phenyl or benzyl; and m is 1;

preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Most preferably, said peptidic compound to be reacted comprises only one guanidino moiety.

In a preferred embodiment, said peptidic compound to be reacted is N-α-benzyloxycarbonyl-L-arginine (Z-Arg-OH).

In an even more preferred embodiment, the peptidic compound to be reacted is Z-Arg-OH; $R^1$ and $R^2$ of the compound of formula (II) are methyl, $R^3$ of the compound of formula (II) is hydrogen and X of the compound of formula (II) is chlorine, thus affording N-α-benzyloxycarbonyl-N-ω-(1,2-dimethylindole-3-sulfonyl)-L-arginine. For the sake of convenience this compound is abbreviated as Z-Arg(MIS)-OH in the following.

In another preferred embodiment, said peptidic compound comprises at least one amino group, said at least one amino group(s) being the N-terminal amino group or being part of the side chain of an amino acid residue, thus affording said peptidic compound, which comprises at least one moiety of the formula (III), wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; and $R^3$ is hydrogen, halogen, $C_{1-6}$ alkyl, $C_{1-6}$ alkoxy, $C_{1-6}$ alkylthio, phenyl or benzyl; and m is 0;

preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Most preferably, said peptidic compound to be reacted comprises only one amino group which is the N-terminal amino group or which is part of the side chain of an amino acid residue.

Even more preferably, the amino group of said peptidic compound to be reacted is the N-terminal amino group.

In a preferred embodiment, said peptidic compound to be reacted is L-alanine methyl ester (H-Ala-OMe).

In an even more preferred embodiment, the peptidic compound is H-Ala-OMe; $R^1$ and $R^2$ of the compound of formula (II) are methyl, $R^3$ of the compound of formula (II) is hydrogen and X of the compound of formula (II) is chlorine, thus affording N-α-(1,2-dimethylindole-3-sulfonyl)-L-alanine methyl ester. For the sake of convenience this compound is abbreviated as MIS-Ala-OMe in the following.

Also even more preferably, the amino group of said peptidic compound to be reacted is part of the side chain of an amino acid residue. Most preferably, said amino group is part of a lysine, homolysine or norlysine residue.

As solvent for the protection process, any inert liquid solvent which can dissolve the reactants may be used. Applicable solvents include halogenated hydrocarbons such as dichloromethane, carbon tetrachloride and dichloroethane; ethers such as diethyl ether, tetrahydrofuran, 2-methyltetrahydrofuran; carboxylic esters and lactones such as ethyl acetate, methyl acetate and valerolactone; and organic solvents containing heteroatoms such as acetone, acetonitrile, dimethylformamide and dimethyl sulfoxide. The solvents can be used alone or as mixtures. Optionally, the solvent or solvent mixture may contain water if the solubility of the reactants requires the presence of water. Preferred solvents are dichloromethane and acetone, alone or in the presence of water.

Optionally, the reaction mixture may contain inorganic or organic bases. Examples for inorganic bases are sodium hydroxide, potassium hydroxide, lithium hydroxide and sodium carbonate. Examples for organic bases are diisopropylethylamine, pyridine and triethylamine. Preferred bases are sodium hydroxide and diisopropylethylamine.

The amount of the compound of formula (II) varies with the reactor volume and can be at a molar ratio from 0.9:1 to 4:1, preferably from 1:1 to 3:1, relative to the organic compound, which comprises at least one guanidino moiety and/or one amino group. The compound of formula (II) may be added in portions to the reaction mixture.

The protection process may be carried out at low or slightly elevated temperatures. For example, a suitable temperature range is from −10° C. to 30° C., preferably from 0° C. to room temperature.

The reaction time depends on different factors like the temperature or the molar ratio of the compound of formula (II) and the organic compound, which comprises at least one guanidino moiety and/or one amino group. Therefore, the reaction may be completed within a few minutes or several hours.

In a further aspect, the present invention relates to an organic compound comprising at least one moiety of the formula

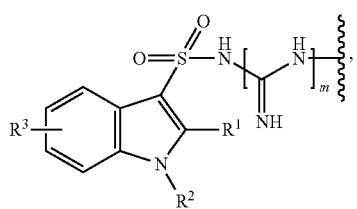

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and m is 0 or 1.

In one embodiment, m is 1, so that the organic compound comprises at least one moiety of the formula

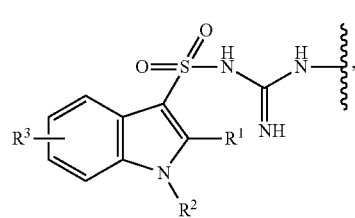

(IV)

wherein $R^1$, $R^2$ and $R^3$ are as defined above.

In another embodiment, m is 0, so that the organic compound comprises at least one moiety of the formula

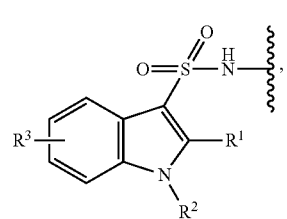

(V)

wherein $R^1$, $R^2$ and $R^3$ are as defined above.

In a preferred embodiment, $R^1$ and $R^2$ are independently $C_{1-4}$ alkyl, $C_{1-4}$ alkoxy or $C_{1-4}$ alkylthio and $R^3$ is hydrogen or halogen. In one embodiment, m is 1 and in another embodiment, m is 0.

In a more preferred embodiment, $R^1$ and $R^2$ are methyl, $R^3$ is hydrogen and X is chlorine. In one embodiment, m is 1 and in another embodiment, m is 0.

In another preferred embodiment, the organic compound is an optionally resin-bound peptidic compound which is optionally side chain protected and/or protected at a free terminus and which comprises at least one moiety of the formula

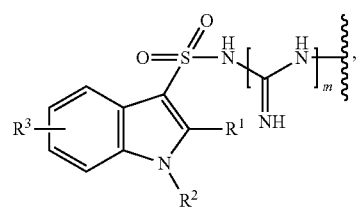

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and m is 0 or 1, preferably m is 1.

Preferably, $R^1$ and $R^2$ are independently $C_{1-4}$ alkyl, $C_{1-4}$ alkoxy or $C_{1-4}$ alkylthio and $R^3$ is hydrogen or halogen. Most preferably, $R^1$ and $R^2$ are methyl and $R^3$ is hydrogen.

In a preferred embodiment, said peptidic compound comprises at least one guanidino moiety being part of an arginine, homoarginine or norarginine residue, preferably being part of an arginine or homoarginine residue, comprising at least one moiety of the formula (III), wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; and $R^3$ is hydrogen, halogen, $C_{1-6}$ alkyl, $C_{1-6}$ alkoxy, $C_{1-6}$ alkylthio, phenyl or benzyl; and m is 1;

preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Most preferably, said peptidic compound comprises only one guanidino moiety.

Even more preferably, said peptidic compound is Z-Arg (MIS)-OH.

In another preferred embodiment, said peptidic compound comprises at least one amino group, said at least one amino group(s) being the N-terminal amino group or being part of the side chain of an amino acid residue, comprising at least one moiety of the formula (III), wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; and $R^3$ is hydrogen, halogen, $C_{1-6}$ alkyl, $C_{1-6}$ alkoxy, $C_{1-6}$ alkylthio, phenyl or benzyl; and m is 0;

preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Also more preferably, said peptidic compound comprises only one amino group which is the N-terminal amino group or which is part of the side chain of an amino acid residue.

Even more preferably, the amino group of said peptidic compound is the N-terminal amino group.

Most preferably, said peptidic compound is MIS-Ala-OMe.

Also even more preferably, the amino group of said peptidic compound is part of the side chain of an amino acid residue. Most preferably, said amino group is part of a lysine, homolysine or norlysine residue.

A further aspect of the invention is modifying and/or coupling in following step(s) the organic compound obtained according to the present invention.

As the organic compounds obtained according to the present invention are important building blocks, they can be applied to form organic compounds being useful as e.g. drug substances.

According to the present invention, the organic compound which comprises at least one moiety of the formula

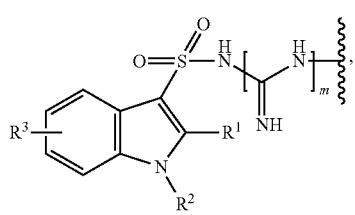

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and m is 0 or 1, is chemically modified in a following step.

In a preferred embodiment, the organic compound to be modified in a following step is an optionally resin-bound peptidic compound which is optionally side chain protected and/or protected at a free terminus and which comprises at least one moiety of the formula (III), wherein $R^1$, $R^2$, $R^3$ and m are as defined above.

Preferably, said peptidic compound comprises at least one guanidino moiety being part of an arginine, homoarginine or norarginine residue, preferably being part of an arginine or homoarginine residue, comprising at least one moiety of the formula (III), wherein $R^1$, $R^2$, $R^3$ and m are as defined above; preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Most preferably, said peptidic compound comprises only one guanidino moiety.

Even more preferably, said peptidic compound is Z-Arg (MIS)-OH.

Modification comprises any organic reaction which complies with the protecting group of the present invention. As an example, Z-Arg(MIS)-OH may be modified by deprotection of the Z group, thus forming H-Arg(MIS)-OH.

Optionally, the modified compound thus obtained is at least once further modified. As an example, H-Arg(MIS)-OH as obtained by a first modification may be further modified by protection of its N-terminus, thus forming e.g. Fmoc-Arg (MIS)-OH.

The deprotection and protection steps can be carried out using reaction conditions known in the art of peptide synthesis.

Also according to the present invention, the organic compound which comprises at least one moiety of the formula

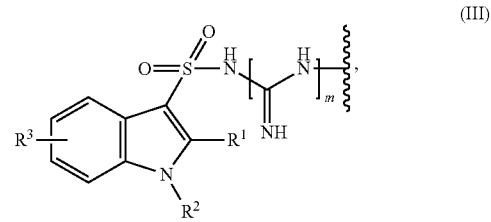

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and m is 0 or 1, is coupled to an organic compound Q in a following step.

Optionally, said coupling step may be repeated at least once and/or at least one further coupling with a suitable coupling compound may be performed. The compound thus obtained may be chemically modified and in case said compound is resin-bound, cleavage from the resin may follow.

In a preferred embodiment, the organic compound to be coupled in a following step to the organic compound Q is an optionally resin-bound peptidic compound which is optionally side chain protected and/or protected at a free terminus and which comprises at least one moiety of the formula (III), wherein $R^1$, $R^2$, $R^3$ and m are as defined above.

Preferably, said peptidic compound comprises at least one guanidino moiety being part of an arginine, homoarginine or norarginine residue, preferably being part of an arginine or homoarginine residue, comprising at least one moiety of the formula (III), wherein $R^1$, $R^2$, $R^3$ and m are as defined above; preferably, wherein $R^1$ and $R^2$ are independently $C_{1-4}$ alkyl, $C_{1-4}$ alkoxy or $C_{1-4}$ alkylthio and $R^3$ is hydrogen or halogen; and more preferably, wherein $R^1$ and $R^2$ are methyl and $R^3$ is hydrogen.

Most preferably, said peptidic compound comprises only one guanidino moiety.

Even more preferably, said peptidic compound is Fmoc-Arg(MIS)-OH or Z-Arg(MIS)-OH.

The organic compound Q is preferably an optionally resin-bound peptidic compound which is optionally side chain protected and/or protected at a free terminus. Most preferably, the organic compound Q is a peptidic compound which is optionally side chain protected and which is optionally resin-bound.

In a preferred embodiment, said peptidic compound is H-Val-resin or H-Trp(Boc)-Ala-Gly-resin, preferably the resin originates from the Sieber amide resin (9-Fmoc-aminoxanthen-3-yloxy-Merrifield resin).

In an even more preferred embodiment, the peptidic compound to be coupled is Fmoc-Arg(MIS)-OH and the peptidic compound to which said peptidic compound is coupled is H-Val-NH-xanthen-3-yloxy-Merrifield resin, thus affording Fmoc-Arg(MIS)-Val-NH-xanthen-3-yloxy-Merrifield resin.

Preferably, said coupling reaction is repeated three times thus affording Fmoc-Arg(MIS)-Arg(MIS)-Arg(MIS)-Arg(MIS)-Val-NH-xanthen-3-yloxy-Merrifield resin (SEQ ID NO 8). Also preferably, Fmoc-Phe-OH is coupled after N-terminal deprotection of said resin-bound peptide, thus affording Fmoc-Phe-Arg(MIS)-Arg(MIS)-Arg(MIS)-Arg(MIS)-Val-NH-xanthen-3-yloxy-Merrifield resin (SEQ ID NO 1). More preferably, the N-terminus is deprotected and acetylated, thus affording Ac-Phe-Arg(MIS)-Arg(MIS)-Arg(MIS)-Arg(MIS)-Val-NH-xanthen-3-yloxy-Merrifield resin (SEQ ID NO 1). Most preferably said resin-bound peptide is cleaved from the resin, thus affording Ac-Phe-Arg(MIS)-Arg(MIS)-Arg(MIS)-Arg(MIS)-Val-NH$_2$ (SEQ ID NO 2).

In an also even more preferred embodiment, the peptidic compound to be coupled is Z-Arg(MIS)-OH and the peptidic compound to which said peptidic compound is coupled is H-Trp(Boc)-Ala-Gly-NH-xanthen-3-yloxy-Merrifield resin, thus affording Z-Arg(MIS)-Trp(Boc)-Ala-Gly-NH-xanthen-3-yloxy-Merrifield resin (SEQ ID NO 3). Preferably, said resin-bound peptide is cleaved from the resin, thus affording Z-Arg(MIS)-Trp(Boc)-Ala-Gly-NH$_2$ (SEQ ID NO 3).

The coupling procedure to the organic compound Q may follow according to any coupling method known to the person skilled in the art. In case the organic compound to be coupled is a peptidic compound, coupling is preferably performed in solid or liquid phase. Most preferably, optionally preceding and optionally following coupling steps are also performed in solid and/or liquid phase.

The term "solid phase" is to be understood to mean solid phase peptide synthesis (SPPS). In SPPS an amino acid or peptide group, optionally protected, is bound to a solid support resin. Then, successive amino acids or peptide groups, optionally protected, are attached to the support-bound peptide until the peptide material of interest is formed. The support-bound peptide is then typically cleaved from the support and subject to further processing and/or purification. In some cases, solid phase synthesis yields a mature peptide product; in other cases the peptide cleaved from the support, i.e. a "peptide intermediate fragment", is used in the preparation of a larger, mature peptidic product.

The term "solution phase" is to be understood to mean solution phase peptide synthesis. In solution phase peptide synthesis, two peptide intermediate fragments, optionally protected, or a peptide intermediate fragment and a reactive amino acid, both optionally protected, are coupled in an appropriate solvent, usually in the presence of additional reagents that promote the efficiency and quality of the coupling reaction. The peptide intermediate fragments are reactively arranged so that the N-terminal of one fragment becomes coupled to the C-terminal of the other fragment, or vice versa. In addition, side chain protecting groups, which are present during solid phase synthesis, are commonly retained on the fragments during solution phase coupling to ensure the specific reactivity of the terminal ends of the fragments. These side chain protecting groups are typically not removed until a mature peptidic compound has been formed.

A further aspect of the invention is the cleavage of an organic compound, comprising at least one moiety of the formula

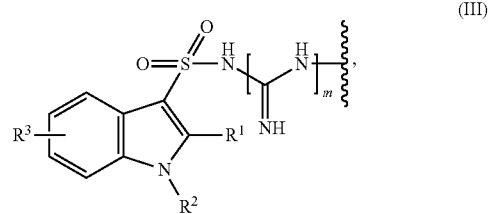

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and m is 0 or 1, said cleavage optionally taking place in the presence of at least one scavenger.

In a preferred embodiment, the cleavage procedure is performed by use of an acid, preferably by use of trifluoroacetic acid (TFA). The acid is applied neat or as mixture with an inert solvent.

An example for a suitable inert solvent is dichloromethane (DCM). Preferably, the molar ratio of acid and solvent is in the range from 1:0 and 1:2, preferably from 1:0 and 1:1.

After cleavage, the formed sulfonylium compound may be trapped by any suitable scavenger. Examples for scavengers are triisopropylsilane (TIS), water, dimethyl sulfide, $C_{1-4}$ alkoxybenzenes such as 1,3,5-trimethoxybenzene (TMB) and $C_{1-4}$ alkoxyphenols such as 3,4-dimethoxyphenol and 3,5-dimethoxyphenol. The scavenger may be used alone or as mixture such as water/TIS.

Preferably, $C_{1-4}$ alkoxybenzenes and $C_{1-4}$ alkoxyphenols are used as scavengers as they are less polar nucleophiles compared to e.g. water. As a consequence, the adducts thus obtained are easier to separate from the target compound in the following work-up procedure.

In a preferred embodiment, said organic compound to be cleaved is an optionally resin-bound peptidic compound which is optionally side chain protected and/or protected at a free terminus. Preferably, $R^1$ and $R^2$ are independently $C_{1-4}$ alkyl, $C_{1-4}$ alkoxy or $C_{1-4}$ alkylthio and $R^3$ is hydrogen or halogen, most preferably, $R^1$ and $R^2$ are methyl and $R^3$ is hydrogen.

In a more preferred embodiment, said peptidic compound to be cleaved is Ac-Phe-Arg(MIS)-Arg(MIS)-Arg(MIS)-Arg(MIS)-Val-NH-xanthen-3-yloxy-Merrifield resin (SEQ ID NO 1), thus affording Ac-Phe-Arg-Arg-Arg-Arg-Val-NH$_2$ (SEQ ID NO 2). Preferably, TFA/DCM/TIS/water is applied as cleavage solution, most preferably in a molar ratio of 50:45:2.5:2.5. Also preferably, TFA/DCM/3,4-dimethoxyphenol is applied as cleavage solution, most preferably in a molar ratio of 50:40:10. Also preferably, TFA/DCM/3,5-dimethoxyphenol is applied as cleavage solution, most preferably in a molar ratio of 50:40:10. Also preferably, TFA/DCM/TMB is applied as cleavage solution, most preferably in a molar ratio of 50:40:10.

In an also more preferred embodiment, said peptidic compound to be cleaved is Z-Arg(MIS)-Trp(Boc)-Ala-Gly-NH-xanthen-3-yloxy-Merrifield resin (SEQ ID NO 3), thus affording Z-Arg-Trp-Ala-Gly-NH$_2$ (SEQ ID NO 4). Preferably, TFA/DCM/TMB is applied as cleavage solution, most preferably in a molar ratio of 50:40:10.

In an also more preferred embodiment, said peptidic compound to be cleaved is MIS-Ala-OMe, thus affording H-Ala-OMe. Preferably, TFA/dimethyl sulfide is applied as cleavage solution, most preferably in a molar ratio of 90:10.

EXAMPLES

The following examples further illustrate this invention but are not intended to limit it in any way. Examples 1 to 8 refer to preparation procedures and Examples 9 to 20 refer to removal assays.

If not indicated otherwise, the L-enantiomer of the amino acid residue was used and all reagents were obtained commercially.

Abbreviations:
Boc=tert-butoxycarbonyl
DIC=diisopropylcarbodiimide
DIPEA=diisopropylethylamine
ESMS=electrospray mass spectrometry
Fmoc=fluoren-9-ylmethoxycarbonyl
HOAt=N-hydroxy-7-azabenzotriazole
HOBt=N-hydroxybenzotriazole
HRMS (CI)=high resolution mass spectrometry (chemical ionization)
MALDI-TOF=matrix-assisted laser desorption ionization-time of flight
MIS=1,2-dimethylindol-3-sulfonyl
PyBOP=benzotriazol-1-yloxy-tripyrrolidinophosphonium hexafluorophosphate
TFA=trifluoroacetic acid
TIS=triisopropylsilane
TMB=1,3,5-trimethoxybenzene
Z-OSu=N-(benzyloxycarbonyloxy)succinimide Example 1

Preparation of pyridinium 1,2-dimethylindole-3-sulfonate 1,2-Dimethylindole (19.7 g, 135.9 mmol) and sulfur trioxide pyridine complex (20.4 g, 128.3 mmol) were dissolved in pyridine (100 mL) under argon atmosphere. The reaction mixture was refluxed for 40 hours and then cooled down to room temperature. After addition of water (400 mL), the resulting solution was washed four times with diethyl ether (each 250 mL). The aqueous phase was evaporated to dryness and dried in the vacuum desiccator to render pyridinium 1,2-dimethylindole-3-sulfonate as red oil (37.6 g, 96% yield).

$^1$H NMR (400 MHz, D$_2$O): δ=8.44 (d, 2H, J=5.8 Hz), 8.31 (m, 1H), 7.75 (m, 2H), 7.67 (d, 1H, J=7.7 Hz), 7.14 (d, 1H, J=7.4 Hz), 7.05 (m, 2H), 3.38 (s, 3H), 2.41 (s, 3H).

$^{13}$C NMR (100 MHz, D$_2$O): δ=147.0, 140.9, 139.2, 135.6, 127.3, 124.1, 122.0, 121.0, 119.2, 112.8, 109.9, 29.2, 10.4.

HRMS (CI): m/z calc. for C$_{10}$H$_{10}$NO$_3$S [M−H]$^+$ 224.0386. found 224.0388.

Example 2

Preparation of 1,2-dimethylindole-3-sulfonyl chloride (MIS-Cl)

Pyridinium 1,2-dimethylindole-3-sulfonate of Example 1 (16.4 g, 53.7 mmol) was suspended in dry dichloromethane (120 mL) under nitrogen atmosphere. The solution was cooled in an ice bath and oxalyl chloride (14 mL, 161 mmol) was slowly added. Then, N,N-dimethylformamide (0.5 mL) was very slowly added under stirring. The reaction mixture was stirred for further 30 minutes in the ice bath and then at room temperature. After 6 hours, the solution was cooled down in an ice bath. Extra oxalyl chloride (4 mL, 46 mmol) and N,N-dimethylformamide (0.4 mL) were added and the reaction mixture was stirred at room temperature for further 15 hours. After addition of oxalyl chloride (2 mL, 23 mmol) and further stirring for 4 hours, the reaction was completed (measured by HPLC; prior measurement, treatment of a small aliquot with methanol for 20 minutes).

The reaction mixture was evaporated to dryness at room temperature. N,N-dimethylformamide (200 mL) was added, followed by water (100 mL). The mixture was stirred for 5 minutes to remove the oxalyl chloride. Then, the phases were separated and the organic phase was washed three times with water (each 100 mL). The organic phase was dried over anhydrous magnesium sulfate and evaporated to dryness affording 1,2-dimethylindole-3-sulfonyl chloride (MIS-Cl) as purple solid (10.2 g, 78% yield).

$^1$H NMR (400 MHz, DMSO): δ=7.82 (d, 1H, J=7.8 Hz), 7.36 (d, 1H, J=8.0 Hz), 7.08 (m, 2H), 7.00 (m, 2H), 3.63 (s, 3H), 2.56 (s, 3H).

$^{13}$C NMR (100 MHz, DMSO): δ=137.2, 135.9, 125.5, 121.4, 120.8, 120.1, 109.7, 30.0, 11.3.

HRMS (CI): m/z calc. for C$_{10}$H$_{10}$NO$_2$S [M−Cl]$^+$ 208.0426. found 208.0427.

Example 3

Preparation of Z-Arg(MIS)-OH

Z-Arg-OH (2 g, 6.5 mmol) was dissolved in acetone (65 mL) and 3N aqueous sodium hydroxide solution (18 mL, 54 mmol). The reaction was cooled in an ice bath and MIS-Cl of Example 2 (1.59 g, 6.5 mmol), dissolved in acetone (50 mL), was added during 10 minutes. The reaction mixture was stirred for 1 hour at 0° C. Then, additional MIS-Cl (0.95 g, 3.9 mmol) in acetone (20 mL) was added, followed by stirring for 90 minutes at 0° C. Finally, a last portion of MIS-Cl (0.95 g, 3.9 mmol) in acetone (15 mL) was added. The reaction mixture was stirred for additional 30 minutes at 0° C. and further 3 hours at room temperature, until no MIS-Cl was detected by TLC (hexane:ethyl acetate 1:1). The pH of the reaction was neutralized with 10% aqueous citric acid. After evaporation of the acetone in vacuo, water (100 mL) was added and the pH was acidified to pH 3 with 10% aqueous citric acid. Then, the solution was three times extracted with ethyl acetate (each 100 mL). The organic phases were put together, washed three times with water (each 75 mL), dried over magnesium sulfate and finally evaporated to dryness. The crude obtained was purified twice by column chromatography (dichloromethane, methanol, acetic acid). The pure fractions were combined and the solvent was removed in vacuo yielding an oil. For precipitation, the minimum amount of a mixture of ethyl acetate, dichloromethane and methanol was added followed by addition of hexane until no further precipitation was observed. The solvent was decanted and the solid was washed four times with a mixture of dichloromethane and hexane and finally dried over magnesium sulfate yielding 18% (0.61 g) of Z-Arg (MIS)-OH.

$^1$H NMR (400 MHz, DMSO): δ=7.85 (d, 1H, J=7.6 Hz), 7.52 (d, 1H, J=8.0 Hz), 7.43 (d, 1H, J=8.0 Hz), 7.30 (m, 5H), 7.10 (m, 2H), 5.01 (s, 2H), 3.87 (m, 1H), 3.66 (s, 3H), 3.0 (m, 2H), 2.60 (s, 3H), 1.64 (m, 1H), 1.49 (m, 1H), 1.41 (m, 2H).

$^{13}$C NMR (100 MHz, DMSO): δ=174.4, 157.0, 156.8, 139.4, 137.7, 135.9, 129.0, 128.5, 128.4, 125.2, 122.1, 121.1, 120.1, 110.4, 66.1, 54.3, 40.0, 30.2, 28.9, 26.4, 11.4.

HRMS (CI): m/z calc. for $C_{24}H_{30}N_5O_6S$ [M+H]$^+$ 516.1911. found 516.1911.

Example 4

Preparation of Fmoc-Arg(MIS)-OH

1. Preparation of H-Arg(MIS)-OH

A mixture of Z-Arg(MIS)-OH as obtained from Example 3 (486 mg, 0.94 mmol) and 10% Pd/C (110 mg) in methanol (60 mL) was hydrogenated overnight at atmospheric pressure. As the reaction was still incomplete (measured by TLC; dichloromethane:methanol:acetic acid, 90:9:1), 10% Pd/C (100 mg) was added and the reaction was hydrogenated for further 24 hours till completeness (measured by TLC). The reaction mixture was filtered over celite and evaporated to dryness yielding 98% (352 mg) of H-Arg(MIS)-OH.

$^1$H NMR (400 MHz, DMSO): δ=7.83 (d, 1H, J=7.6 Hz), 7.47 (d, 1H, J=8.1 Hz), 7.42 (d, 1H, J=8.1 Hz), 7.11 (m, 2H), 3.65 (s, 3H), 3.17 (m, 1H), 3.00 (m, 2H), 2.60 (s, 3H), 1.65 (m, 1H), 1.54 (m, 1H), 1.42 (m, 2H).

2. Preparation of Fmoc-Arg(MIS)-OH

Fmoc-Cl (84 mg, 0.32 mmol) was dissolved in 1,4-dioxane (0.5 mL). Sodium azide (25 mg, 0.39 mmol) in water (0.4 mL) was added and the resulting emulsion was stirred for 2 hours at room temperature. Then, the emulsion was slowly added to a solution of H-Arg(MIS)-OH as obtained in the previous step (136 mg, 0.36 mmol) in a 1:1 mixture of water and dioxane at pH 9, which was controlled by addition of 10% aqueous sodium carbonate. The reaction mixture was stirred while keeping the pH at 9. Once the pH was stabilized, the mixture was stirred overnight. Then, water (30 mL) was added and the mixture was washed three times with tert-butyl methyl ether (each 20 mL). The aqueous phase was acidified with 1N HCl to a pH of 2 to 3 and was then quickly extracted three times with ethyl acetate (30 mL). The organic phases were combined and dried over magnesium sulfate. After evaporation to dryness, an oil (115 mg) was obtained, which was dissolved in a minimum of acetone. Then, aqueous sodium carbonate (20 mL) was added at pH 9 and the aqueous solution was washed three times with tert-butyl methyl ether (each 30 mL). The aqueous solution thus obtained was acidified with 1N HCl to a pH of 2 to 3, then extracted three times with ethyl acetate (each 20 mL), dried over magnesium sulfate and finally evaporated to dryness yielding 34.3% (67.4 mg) of Fmoc-Arg(MIS)-OH.

$^1$H NMR (400 MHz, DMSO): δ=7.86 (m, 3H), 7.70 (d, 2H, J=7.4 Hz), 7.59 (d, 1H, J=7.9 Hz), 7.42 (d, 1H, J=8.1 Hz), 7.39 (m, 2H), 7.30 (m, 2H), 7.10 (m, 2H), 4.27 (m, 2H), 4.20 (m, 1H), 3.86 (m, 1H), 3.66 (s, 3H), 3.01 (m, 2H), 2.61 (s, 3H), 1.65 (m, 1H), 1.52 (m, 1H), 1.38 (m, 2H).

$^{13}$C NMR (100 MHz, DMSO): δ=174.4, 157.0, 156.8, 144.5, 141.4, 139.4, 135.9, 128.3, 127.8, 126.0, 125.2, 122.1, 121.1, 120.8, 120.1, 110.4, 66.3, 55.6, 47.3, 40.0, 30.2, 28.8, 26.5, 11.4.

HRMS (CI): m/z calc. for $C_{31}H_{34}N_5O_6S$ [M+H]$^+$ 604.2224. found 604.2222.

Example 5

Preparation of Ac-Phe-Arg(MIS)-Arg(MIS)-Arg(MIS)-Arg(MIS)-Val-NH$_2$ (SEQ ID NO 2)

Sieber amide resin (25 mg, 0.42 mmol/g, 9-Fmoc-aminoxanthen-3-yloxy-Merrifield resin) was placed in a 2 mL polypropylene syringe fitted with a polyethylene filter disk. The resin was swollen with dichloromethane. Subsequently, washings with dichloromethane and N,N-dimethylformamide were carried out and the Fmoc group was removed by treatment with a 2:8 mixture of piperidine and N,N-dimethylformamide (once for 1 minute, and two times for 10 minutes). Fmoc-Val-OH (14.3 mg, 42.1 μmol) was coupled using HOBt (5.7 mg, 42.1 μmol) and DIC (6.7 μL, 42.1 μmol) in N,N-dimethylformamide for 1.5 hours. The Fmoc group was removed in the usual way, and Fmoc-Arg(MIS)-OH as obtained from Example 4 (15.8 mg, 26.3 μmol) was coupled using PyBOP (13.7 mg, 26.3 μmol), HOAt (3.6 mg, 26.3 μmol) and DIPEA (13.4 μL, 78.9 μmol) in N,N-dimethylformamide for 90 minutes. The resin was acetylated by treatment with acetic anhydride (50 eq) and DIPEA (50 eq) in DMF for 25 min in order to do the capping of the unreacted amines, the Fmoc group was removed and the same procedure was repeated three more times including acetylation of the resin prior to Fmoc removal. After the last Fmoc removal, Fmoc-Phe-OH (13.6 mg, 35 μmol) was coupled using PyBOP (18.3 mg, 35 μmol), HOAt (4.8 mg, 35 μmol) and DIPEA (17.9 μL, 105.2 μmol) in N,N-dimethylformamide for 90 min. The Fmoc group was removed, and the resulting free amino group was acetylated in the same way as described above. The protected, resin-bound peptide Ac-Phe-Arg(MIS)-Arg(MIS)-Arg(MIS)-Arg(MIS)-Val-NH-xanthen-3-yloxy-Merrifield resin thus obtained was washed with N,N-dimethylformamide, dichloromethane and diethyl ether, dried in vacuo and then divided into five aliquots.

One aliquot was used for the preparation of the target compound of this example and the other aliquots were used as starting material for the removal assays of e.g. Example 9.

Thus, one aliquot was swollen with dichloromethane and treated with 1.5 mL of a mixture of TFA, dichloromethane, TIS and water (2:93:2.5:2.5) for 20 minutes in order to cleave the protected peptide from the resin. The resin was filtered and the collected solution was diluted with dichloromethane and neutralized by adding DIPEA (80 μL, 1.2 eq per eq of TFA). The solvent was removed in vacuo. After addition of water and acetonitrile, the solution was lyophilized obtaining Ac-Phe-Arg(MIS)-Arg(MIS)-Arg(MIS)-Arg(MIS)-Val-NH$_2$ (SEQ ID NO 2).

The product was characterized by LC-MS and HRMS (CI): m/z calc. for $C_{80}H_{107}N_{23}O_{15}S_4$ [M+Na]$^+$ 1780.7092. found 1780.7152.

Example 6

Preparation of Z-Arg(MIS)-Trp(Boc)-Ala-Gly-NH$_2$ (SEQ ID NO 4)

Sieber amide resin (70 mg, 0.40 mmol/g) was placed in a 2 mL polypropylene syringe fitted with a polyethylene filter disk. The resin was swollen with dichloromethane, washings with dichloromethane and N,N-dimethylformamide were carried out and the Fmoc group was removed. Fmoc-Gly-OH (33.3 mg, 112 µmol), Fmoc-Ala-OH (34.9 mg, 112 µmol) and Fmoc-Trp(Boc)-OH (59.0 mg, 112 µmol) were sequentially coupled using PyBOP (58.3 mg, 112 µmol) HOAt (15.2 mg, 112 µmol) and DIPEA (57.4 µL, 336 µmol) in N,N-dimethylformamide for 1.5 hours. The resin was divided into two equal parts. One part was used for the preparation of the target compound of this example and the other part for the preparation of Z-Arg(Pbf)-Trp(Boc)-Ala-Gly-NH$_2$ (see Example 8.2).

Thus, Z-Arg(MIS)-OH (28.9 mg, 56 µmol) was coupled with one resin part using PyBOP (29.2 mg, 56 µmol), HOAt (7.6 mg, 56 µmol) and DIPEA (28.7 µL, 168 µmol) in N,N-dimethylformamide for 1.5 hours. The protected, resin-bound peptide Z-Arg(MIS)-Trp(Boc)-Ala-Gly-NH-xanthen-3-yloxy-Merrifield resin thus obtained was washed with N,N-dimethylformamide, dichloromethane and diethyl ether, dried in vacuo and then divided into aliquots of 4 mg. One aliquot was used for the preparation of the target compound of this example and the other aliquots were used as starting material for the removal assays of e.g. Example 19.

Thus, one aliquot was swollen with dichloromethane and treated with 1.5 mL of a mixture of TFA, dichloromethane, TIS and water (2:93:2.5:2.5) for 20 minutes in order to cleave the protected peptide from the resin. The resin was filtered and the collected solution was diluted with dichloromethane and neutralized by adding DIPEA (80 µL, 1.2 eq per eq of TFA). The solvent was removed in vacuo. After addition of water and acetonitrile, the solution was lyophilized obtaining Z-Arg(MIS)-Trp(Boc)-Ala-Gly-NH$_2$ with 95% purity (by HPLC). The product obtained was characterized by LC-MS.

Example 7

Preparation of MIS-Ala-OMe

H-Ala-OMe (95 mg, 0.68 mmol, 1 eq) was dissolved in dry dichloromethane and DIPEA (3 eq) was added. A solution of MIS-Cl (200 mg, 1.2 eq), as obtained from Example 2, in dry dichloromethane was added, and the reaction mixture was stirred for 1.5 hours at room temperature. Work up in the usual way yielded 85.4 mg (40%) of MIS-Ala-OMe.

Example 8

Preparation of the Pbf Protected Comparison Compounds

8.1 Preparation of Ac-Phe-Arg(Pbf)-Arg(Pbf)-Arg(Pbf)-Arg(Pbf)-Val-NH$_2$ (SEQ ID NO 2)

The same procedure as for the preparation of Ac-Phe-Arg(MIS)-Arg(MIS)-Arg(MIS)-Arg(MIS)-Val-NH$_2$ was applied (see Example 5) except for replacing Fmoc-Arg(MIS)-OH by Fmoc-Arg(Pbf)-OH (17.1 mg, 26.3 µmol). The product obtained was characterized by LC-MS and HRMS (CI): m/z calc. for $C_{92}H_{136}N_{19}O_{19}S_4$ [M+H]$^+$ 1938.9137. found 1938.9202.

8.2 Preparation of Z-Arg(Pbf)-Trp(Boc)-Ala-Gly-NH, (SEQ ID NO 4)

Fmoc-Arg(Pbf)-OH (36.3 mg, 56 µmol) was coupled with the other resin part from Example 6 using PyBOP (29.2 mg, 56 µmol), HOAt (7.6 mg, 56 µmol) and DIPEA (28.7 µL, 168 µmol) in N,N-dimethylformamide for 1.5 hours. The Fmoc group was removed and the free amine was protected with the Z group by treatment with Z-OSu (14.0 mg, 56 µmol) and DIPEA (35.9 µL, 210 µmol). The protected, resin-bound peptide Z-Arg(Pbf)-Trp(Boc)-Ala-Gly-NH-xanthen-3-yloxy-Merrifield resin thus obtained was washed with N,N-dimethylformamide, dichloromethane and diethyl ether, dried in vacuo, and then divided into aliquots of 4 mg.

One aliquot was used for the preparation of the target compound of this example and the other aliquots were used as starting material for the removal assay of e.g. Example 20.

Thus, one aliquot was cleaved in the same way as described in Example 5. Z-Arg(Pbf)-Trp(Boc)-Ala-Gly-NH$_2$ was obtained with 96% purity (by HPLC). The product was characterized by LC-MS.

8.3 Preparation of Pbf-Ala-OMe

Preparation was performed analogous to Example 7 except for Pbf-Cl (1.2 eq) instead of MIS-Cl. Yield: 209 mg (82%) of Pbf-Ala-OMe.

Examples 9 to 12

Removal Assays of MIS Versus Pbf Protected, Resin-Bound Peptides

General Procedure

The protected, resin-bound peptide (3 mg) was treated with cleavage solution (50 µL). After the cleavage time, the solution was poured into water (4 mL). Then, TFA and dichloromethane were evaporated. The resulting aqueous solution was washed six times with dichloromethane (each 1 mL) and lyophilized. The resulting solid was analyzed by HPLC ($\lambda$=220 nm) and ESMS or MALDI-TOF.

TABLE 1

| Examples 9 to 12 with cleavage solution TFA/DCM/TIS/water (50:45:2.5:2.5) (water and TIS as scavengers) | | | |
|---|---|---|---|
| Example | Protected, resin bound peptide | Cleavage time | Ac-Phe-Arg-Arg-Arg-Arg-Val-NH$_2$ (SEQ ID NO 2) |
| 9 | a | 30 min | 100% |
| 10 | a | 60 min | 100% |
| 11 | b | 30 min | 4% |
| 12 | b | 60 min | 38% | a = Ac-Phe-Arg(MIS)-Arg(MIS)-Arg(MIS)-Arg(MIS)-Val-NH-xanthen-3-yloxy-Merrifield resin (SEQ ID NO 1) as obtained from Example 5.
b = Ac-Phe-Arg(Pbf)-Arg(Pbf)-Arg(Pbf)-Arg(Pbf)-Val-NH-xanthen-3-yloxy-Merrifield resin (SEQ ID NO 1) as obtained from Example 8.1 (comparison example).
DCM = Dichloromethane.

Examples 13 to 15

Removal Assays of MIS Protected, Resin-Bound Peptides with Different Scavengers The general procedure as described in Examples 9 to 12 was followed. As protected, resin-bound peptide Ac-Phe-Arg(MIS)-Arg(MIS)-Arg(MIS)-Arg(MIS)-Val-NH-xanthen-3-yloxy-Merrifield resin (SEQ ID NO 1), as obtained from Example 5, was used. The cleavage time was 60 minutes. A mixture of TFA, dichloromethane and scavenger (50:40:10) was used as cleavage solution.

The scavengers tested were 3,4-dimethoxyphenol (Example 13), 1,3,5-trimethoxybenzene (TMB) (Example 14) and 3,5-dimethoxyphenol (Example 15).

As a result, the amount of MIS-OH was reduced by more than 10 times compared to Example 9, in which water (2.5%) and TIS (2.5%) were used as scavengers. In the case of Tmb, a reduction by more than 40 times was even observed.

Examples 16 and 17

Removal Assays of MIS Versus Pbf Protected, Resin-Bound, Trp-Containing Peptides The general procedure as described in Examples 9 to 12 was followed. The resulting crudes were characterized by LC-MS and its purity was analyzed by HPLC ($\lambda$=220 nm).

The purity of the resulted crude was higher for the MIS protected starting material compared to the Pbf protected starting material. For both protected peptides c and d, neither undesired Trp alkylation nor sulfonation was observed in the formed product.

TABLE 2

Examples 16 and 17; with cleavage solution TFA/DCM/TMB (50:40:10) (TMB as scavenger)

| Example | Protected, resin bound peptide | Cleavage time | Z-Arg-Trp-Ala-Gly-NH$_2$ (SEQ ID NO 4) |
|---|---|---|---|
| 16 | c | 60 min | 83.4%♣ |
| 17 | d | 60 min | 63.4%* | c = Z-Arg(MIS)-Trp(Boc)-Ala-Gly-NH-xanthen-3-yloxy-Merrifield resin (SEQ ID NO 3) as obtained from Example 6.
d = Z-Arg(Pbf)-Trp(Boc)-Ala-Gly-NH-xanthen-3-yloxy-Merrifield resin (SEQ ID NO 3) as obtained from Example 8.2 (comparison example).
DCM = Dichloromethane
TMB = 1,3,5-trimethoxybenzene ♣Z-Arg(MIS)-Trp-Ala-Gly-NH$_2$ (SEQ ID NO 4) was not detected in the resulting crude (by LC-MS)
*20.4% of Z-Arg(Pbf)-Trp-Ala-Gly-NH$_2$ (SEQ ID NO 4) was detected in the resulting crude (by HPLC).

Examples 18 to 20

Removal Assays of MIS Versus Pbf as N$^\alpha$-Amino Protecting Groups

The protected amino acids were treated with the cleavage solution at room temperature and the deprotection was followed by TLC.

MIS removal was slightly faster, presenting a positive Kaiser test (indicating the presence of free amines) after 5 min, whereas for the case of Pbf the positive Kaiser test was in the next control (10 min).

TABLE 3

Examples 18 to 20; with cleavage solution TFA/dimethyl sulfide (90:10) (dimethyl sulfide as scavenger)

| Example | Protected peptide | Cleavage time | H-Ala-OMe♣ |
|---|---|---|---|
| 18 | e | 5 min | detected |
| 19 | f | 5 min | not detected |
| 20 | f | 10 min | detected | e = MIS-Ala-OMe as obtained from Example 7.
f = Pbf-Ala-OMe as obtained from Example 8.3 (comparison example).

♣Presence or absence of H-Ala-OMe was detected by the Kaiser test.

The invention claimed is:

1. A peptidic compound comprising at least one moiety of the formula (III), said formula (III) being defined as follows:

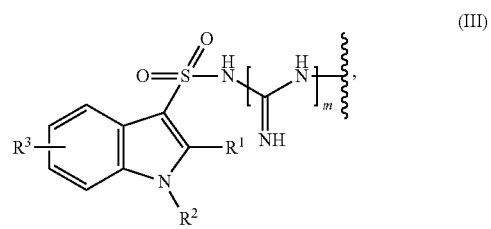

(III)

wherein $R^1$ is hydrogen, $C_{1-6}$ alkyl, $C_{1-6}$ alkoxy or $C_{1-6}$ alkylthio; $R^2$ is $C_{1-6}$ alkyl, $C_{1-6}$ alkoxy or $C_{1-6}$ alkylthio; or $R^1$ and $R^2$ together form a moiety of formula —$(CH_2)_n$—, wherein n is an integer from 3 to 5; $R^3$ is hydrogen, halogen, $C_{1-6}$ alkyl, $C_{1-6}$ alkoxy, $C_{1-6}$ alkylthio, phenyl or benzyl; and wherein m is 0 or 1.

2. The compound of claim 1, wherein the peptidic compound is resin-bound peptidic compound.

3. The compound of claim 1, wherein the peptidic compound is side chain protected and/or protected at a free terminus.

4. The compound of claim 1 wherein said compound is N-alpha-benzyloxycarbonyl-N-omega-(1,2-dimethylindole-3-sulfonyl)-L-arginine.

5. The compound of claim 1 wherein said compound is N-alpha-Fmoc-N-omega-(1,2-dimethylindole-3-sulfonyl)-L-arginine.

6. A process for the preparation of the peptidic compound as defined in claim 1, comprising the step of reacting a peptidic compound having at least one guanidino moiety and/or at least one amino group, with a compound of formula (II), said compound of formula (II) being defined as follows:

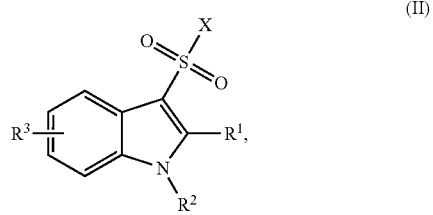

(II)

wherein $R^1$, $R^2$, and $R^3$ are as defined in claim 1, and X is chlorine or bromine.

7. The process of claim 6, wherein $R^1$ and $R^2$ are independently $C_{1-4}$ alkyl, $C_{1-4}$ alkoxy or $C_{1-4}$ alkylthio and $R^3$ is hydrogen or halogen.

8. The process of claim 6, wherein $R^1$ and $R^2$ are methyl, $R^3$ is hydrogen and X is chlorine.

9. The process of claim 6, wherein said peptidic compound having at least one guanidino moiety and/or at least one amino group is a resin-bound peptidic compound.

10. The process of claim 6, wherein said peptidic compound having at least one guanidino moiety and/or at least one amino group is side chain protected and/or protected at a free terminus.

* * * * *